United States Patent [19]

Tahara et al.

[11] Patent Number: 5,021,553

[45] Date of Patent: Jun. 4, 1991

[54] ANTI-HUMAN ADENOCARCINOMA ANTIGEN SPECIFIC MONOCLONAL ANTIBODY

[75] Inventors: Eiichi Tahara; Atsushi Ochiai; Hiroshi Yokozaki; Toyoharu Hozumi; Eikai Kyo, all of Hiroshima, Japan

[73] Assignee: Wakunaga Seiyaku Kabushiki Kaisha, Osaka, Japan

[21] Appl. No.: 377,764

[22] Filed: Jul. 10, 1989

Related U.S. Application Data

[63] Continuation of Ser. No. 790,400, Oct. 23, 1985, abandoned.

[30] Foreign Application Priority Data

Oct. 26, 1984 [JP] Japan ................. 59-223830
Sep. 10, 1985 [JP] Japan ................. 60-198592

[51] Int. Cl.⁵ .............. A61K 39/395; C07K 15/28; C12N 5/02
[52] U.S. Cl. .................... 530/387; 530/388; 530/395; 530/808; 530/828; 435/70.21; 435/240.27; 435/172.2
[58] Field of Search ............. 530/387, 388, 389, 395, 530/808, 828, 806; 424/85.8; 435/7, 240.27, 240.26, 70.21, 172.2

[56] References Cited

U.S. PATENT DOCUMENTS 4,569,788  2/1986  Mulshine et al. ............... 435/172.2
4,579,827  4/1986  Sakamoto et al. .................. 436/536
4,683,200  7/1987  Hirohashi et al. ................. 530/387

FOREIGN PATENT DOCUMENTS 213581  3/1987  European Pat. Off. .
160897  9/1987  European Pat. Off. .

OTHER PUBLICATIONS

Ochiai, A. et al., Jpn. J. Cancer Research, (GANN), 76(10): 915-918 (10-1985), cited in Medline Abstract No. 05784379 (1986).
Ochiai, A., et al., Gan Tokagaku Ryoho, 13 (4 PT2): 1416-1422, (4-1986), cited in Medline Abstract No. 05966838 (1986).
Biological Aspects, vol. 81, No. 44610, 1986.

Primary Examiner—Margaret Moskowitz
Assistant Examiner—Jeff Kushan
Attorney, Agent, or Firm—Wegner, Cantor, Mueller & Player

[57] ABSTRACT

A monoclonal antibody against human cancer, characterized in that the monoclonal antibody is produced by a hybridoma cell line obtained from the fusion of B-lymphocyte immunized with cells of human cancer origin and tumor cells, and reactive with cancer cells from more than one organ but substantially not reactive with normal cells, and a process for production thereof; and a hybridoma cell line used to produce the above-mentioned monoclonal antibody, and a process for production thereof.

2 Claims, 4 Drawing Sheets

ANTI-HUMAN ADENOCARCINOMA ANTIGEN SPECIFIC MONOCLONAL ANTIBODY

This application is a continuation of U.S. application Ser. No. 790,400 filed Oct. 23, 1985, now abandoned.

BACKGROUND OF THE INVENTION

1. Field of the Invention

The present invention relates to monoclonal antibodies capable of reacting with cancer cells from more than one human organ but substantially not reacting with normal cells, a process for production of the monoclonal antibodies, hybridoma cell lines producing the monoclonal antibodies, and a process for production of the cell lines.

2. Description of the Related Art

Since the technique for cell fusion was published (*Nature*, 256, 495-497, 1975), various kinds of monoclonal antibodies have been prepared and studied for application in the diagnosis and therapy of diseases such as cancer. (See, GANN, 75, 485, 1983; *Proc. Natl. Acad. Sci. USA*, 75, 3405, 1978; *Proc. Natl. Acad. Sci. USA*, 76, 1438, 1979; and *Science*, 212, 53 (1981), etc.)

To use a monoclonal antibody for the diagnosis of cancer, the monoclonal antibody must react with or bind to the cancer cells but should not react with or bind to normal cells. In some cases, it is desirable that the monoclonal antibody react with or bind to cancer cells from more than one human organ, so that more than one kind of cancer cell can be simultaneously detected.

However, known monoclonal antibodies against human cancer are substantially reactive with human normal cells. Therefore, there are problems with the prior art monoclonal antibodies when practically used for the diagnosis of cancer.

Japanese Unexamined Patent Publication No. 59-128397 discloses a monoclonal antibody against human stomach cancer, which reacts with well-differentiated stomach cancer cells but which has only a weak reaction with poorly-differentiated stomach cancer cells. This publication does not disclose whether the monoclonal antibody reacts with normal cells.

Therefore, it is strongly desired to provide monoclonal antibodies capable of reacting with cancer cells from more than one human organ but substantially not reacting with normal cells.

SUMMARY OF THE INVENTION

Accordingly, the present inventors decided to carry out research into the production of monoclonal antibodies by using TMK-1 cells, i.e., cells derived from human stomach poorly-differentiated adenocarcinoma cells and transplanted to SC-6-JCK nude mice, as an antigen.

In this connection, the inventors are not aware of any publications disclosing the production of monoclonal antibodies by using TMK-1 cells.

Therefore, an object of the present invention is to provide a monoclonal antibody against human cancer, characterized in that the monoclonal antibody is produced by a hybridoma cell line obtained from the fusion of B-lymphocyte immunized with cells of human cancer origin and tumor cells, and reactive with cancer cells from more than one human organ but substantially not reactive with normal cells.

Another object of the present invention is to provide a process for production of the above-mentioned monoclonal antibody, wherein the above-mentioned hybridoma cells are cultured in a culture medium in vitro or in the body of an animal in which the hybridoma cells can grow, and the monoclonal antibody is recovered from the cultured medium or ascites taken from the animal and optionally purified by a conventional process.

Another object of the present invention is to provide a hybridoma cell line obtained by the fusion of B-lymphocyte immunized with cells of human cancer origin and tumor cells, and capable of producing a monoclonal antibody against human cancer, which monoclonal antibody is reactive with cancer cells from more than one human organ but substantially not reactive with normal cells.

Another object of the present invention is to provide a process for production of the above-mentioned hybridoma cell line, comprising preparing B-lymphocytes immunized with cells of human cancer origin, fusing the B-lymphocyte with tumor cells, and cloning and selecting hybridoma producing a desired monoclonal antibody.

Other objects and advantages of the present invention will be apparent from the description set forth hereinbelow.

DESCRIPTION OF THE PREFERRED EMBODIMNETS

Figure 1:
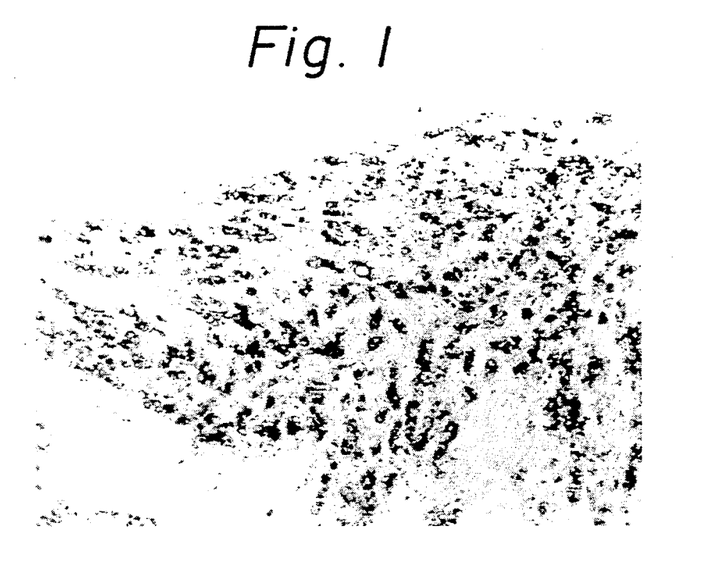
FIG. 1 represents a micrograph at 160 magnifications of stomach cancer cells stained by Avidin-Biotin Peroxidase Complex (ABC) method using a monoclonal antibody produced by hybridoma 9A3, wherein the black portions represent stomach cancer cells.
Figure 2:
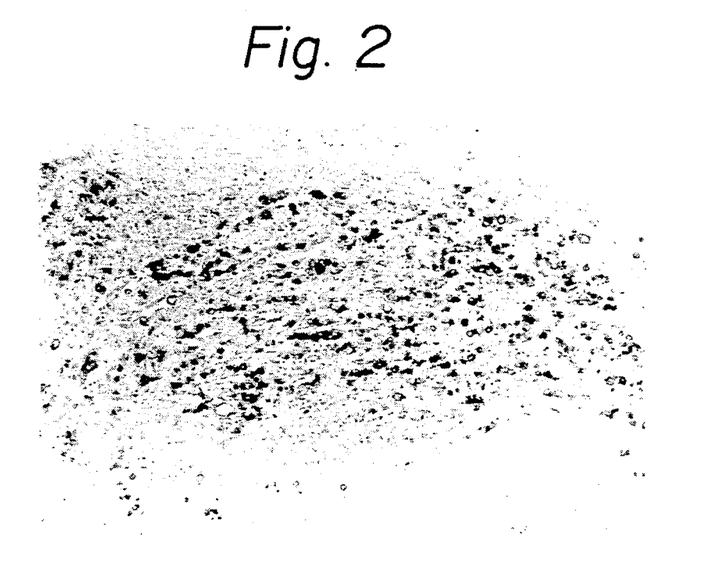
FIG. 2 represents a micrograph at 160 magnifications of stomach cancer cells stained by the ABC method using a monoclonal antibody produced by hybridoma 9A3, wherein the black portions represent stomach cancer cells.
Figure 3:
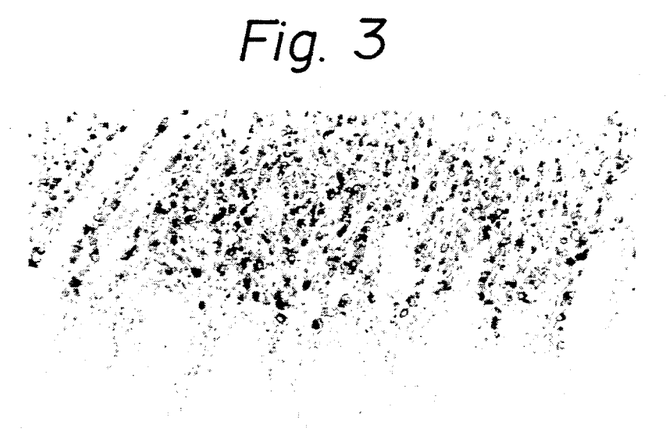
FIG. 3 represents a micrograph at 160 magnifications of signet ring cells (stomach cancer cells) stained by the ABC method using a monoclonal antibody produced by hybridoma 9A3, wherein unstained portions represent normal epidermis and the black portions represent cancer cells.
Figure 4:
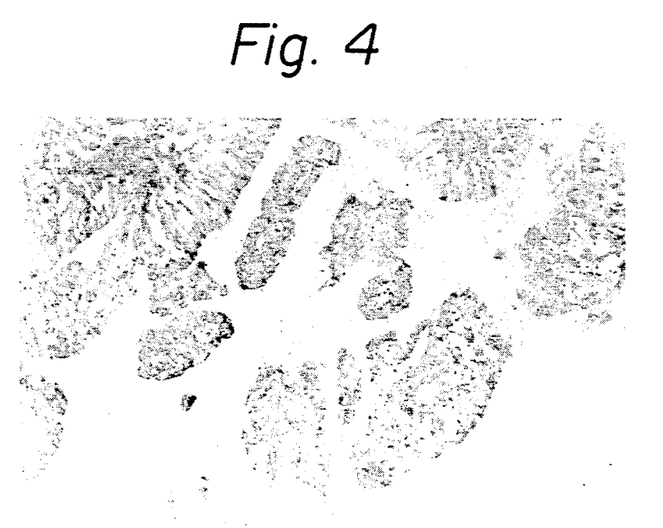
FIG. 4 represents a micrograph at 160 magnifications of papillary adenocarcinoma cells (stomach cancer cells) stained by the ABC method using a monoclonal antibody produced by hybridoma 9A3, wherein the black portions represent cancer cells in which the cytoplasm and cell membrane of the cancer cells are stained.
Figure 5:
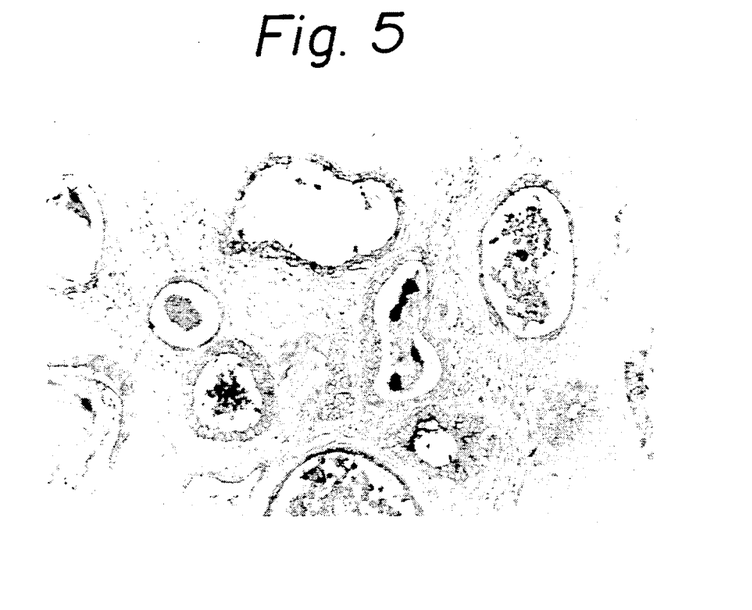
FIG. 5 represents a micrograph at 160 magnifications of well-differentiated tubular adenocarcinoma cells (stomach cancer cells) stained by the ABC method using a monoclonal antibody produced by hybridoma 20D11, wherein the black portions represent cancer cells.
Figure 6:
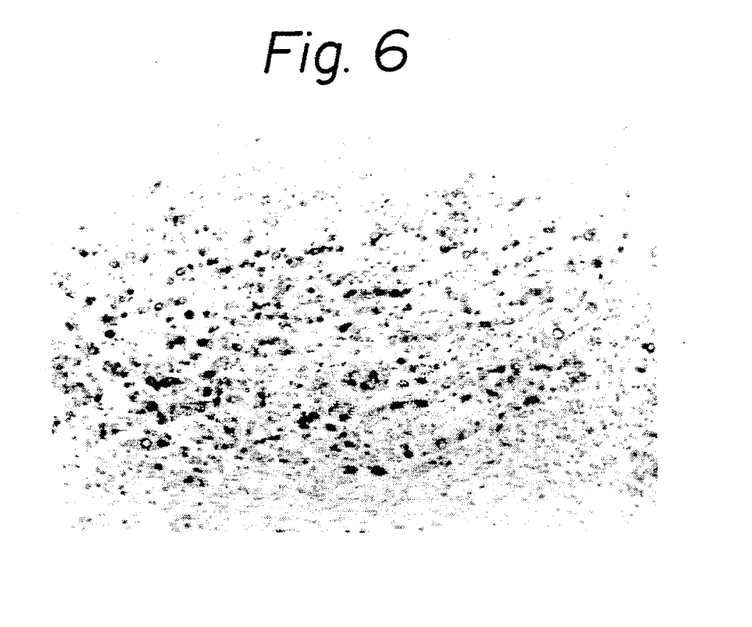
FIG. 6 represents a micrograph at 160 magnifications of poorly-differentiated stomach adenocarcinoma cells stained by the ABC method using a monoclonal antibody produced by hybridoma 20D11, wherein the black portions represent cancer cells.
Figure 7:
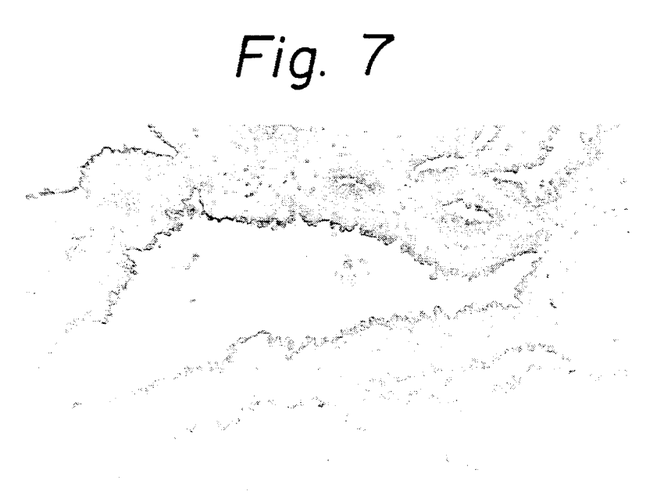
FIG. 7 represents a micrograph at 160 magnifications of alveolar cell carcinoma of lung stained by the ABC method using a monoclonal antibody produced by hybridoma 20D11, wherein the black portions represent cancer cells; and, FIG. 8 represents a micrograph at 160 magnifications of adenocarcinoma of pancreas stained by the ABC method using a monoclonal antibody produced by hybridoma 20D11, wherein the black portions represent cancer cells.
Figure 8:
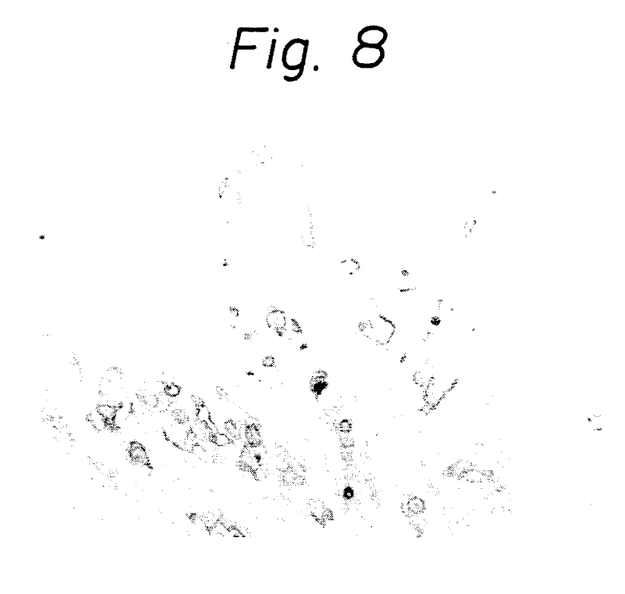

Preparation of Hybridomas and Production of Monoclonal Antibodies

Monoclonal antibodies of the present invention are produced by preparing hybridoma cell lines capable of producing desired antibodies, and culturing the cell lines to obtain the monoclonal antibodies. The cell lines of the present invention are prepared by; (1) preparing antibody-producing cells by immunizing an animal with cells of human cancer origin, (2) fusing the antibody-producing cells with tumor cells to obtain hybridomas capable of producing the monoclonal antibody and immortalized, and (3) cloning and selecting hybridoma producing the desired monoclonal antibody. The desired monoclonal antibody is produced by; (4) culturing the hybridoma in vitro in a culture medium, or in vivo in an animal, and (5) recovering the monoclonal antibody from the cultured medium, or from ascites obtained from the animal. General processes for the preparation of hybridoma and production of monoclonal antibodies are known, and described, for example, in Japanese Examined Patent Publication No. 58-45407, Japanese Unexamined Patent Publication No. 59-128397, and *J. Immunol. Methods*, 39, 285–308 (1980).

(1) Preparation of antibody-producing cells

Antibody-producing cells may be prepared according to any known process as described, for example, in *Methods in Enzymology*, 73, 14 (1981), by immunizing animals with cells of human cancer origin, removing the spleens from the animals, and preparing splenocyte suspension from the spleens. Alternatively, antibody-producing cells can be prepared by obtaining splenocytes from not-immunized animals, and immunizing the splenocytes in vitro with cells of human cancer origin.

Preferably, mice are immunized intraperitoneally with TMK-1 cells and boosted twice every ten days, and after the last boost, the spleens are removed from the immunized mice and antibody-producing cells are prepared from the spleens. The TMK-1 cell line is a tissue culture cell line of SC-6-JCK cells which are transplanted into nude mice from human poorly-differentiated stomach adenocarcinoma cells (see *Gan no Rinsho*, 27, 1605–1612, 1981, Japan).

(2) Cell Fusion

The antibody-producing cells prepared as above are fused with tumor cells in the presence of a fusion agent to form a hybridoma which produces monoclonal antibodies and which is immortalized. The general fusion procedure is well known and described, for example, in *J. Immunol. Methods*, supra; and *Nature*, supra. According to the present invention, preferably, the above-described antibody-producing cells are fused with tumor cells P3-X63-Ag8U$_1$ (P$_3$U1) (*Methods in Enzymol.*, 73, 3–46, 1981) in RPMI-1640 medium in the presence of 40% polyethylene glycol.

(3) Selection of Hybridoma

When tumor cells such as P$_3$U1 are used as the fusion partner, an HAT medium, i.e., RPMI-1640 medium supplemented with hypoxanthine, aminopterin, and thymidine, is used as the fusion medium (*Methods in Enzymol.*, 73, 16–18, 1981). Hybridoma can grow in the HAT medium, but parent cells cannot grow. Supernatants in which hybridoma have been grown are arrayed to detect the presence of the desired monoclonal antibody. The assays are carried out by, for example, the plaque method, agglutination method, radioimmunoassay method, and conveniently, the ELISA method (*Methods in Enzymol.*, 70, 419–439, 1980).

(4) Culturing of Hybridoma for Production of Monoclonal Antibody

Hybridoma prepared as above is cultured in a culture medium such as an RPMI-1640 medium supplemented with 10 to 20% of fetal bovine serum (*Methods in Enzymol.*, 73, 42–43, 1981), or is injected intraperitoneally into an experimental animal such as a rat or mouse in which the hybridoma cells can be grown to culture the cells in vivo (*Methods in Enzymol.*, 73, 43–44, 1981), to produce the monoclonal antibody in the cultured medium or ascites from the animal.

(5) Recovery of the Monoclonal Antibody

The monoclonal antibody produced is recovered from the cultured medium or the ascites according to any conventional method, such as ammonium sulfate precipitation, and purified, for example, by gel filtration, ion exchange chromatography, or affinity column chromatography, or a combination thereof (see, *Monoclonal Antibodies*, 405, 1980, Plenum Press).

Determination of Specificity of the Monoclonal Antibody

The specificity of the monoclonal antibodies prepared according to the present invention is determined by ELISA using cancer cells immobilized on a support. Alternatively, the determination can be carried out by a commercially available kit using tissue preparations of cancer cells. The ABC method (*J. Histochem. Cytochem.*, 29, 577, 1981) can be conveniently carried out using a Vectastain (T.M.) ABC kit. The detailed procedure for determination of the specificity of the present monoclonal antibodies and result thereof are described in Example 2 to 4.

As seen from Table 3, three representative monoclonal antibodies of the present invention produced by hybridoma 9A3, 20D11, and 21A4 do not substantially react with normal cells. Such a property is especially remarkable in monoclonal antibodies produced by hybridomas 9A3 and 20D11.

As seen from Table 2, the present monoclonal antibodies react with various kinds of histological typing of stomach cancer regardless of the extent of differentiation. Such a property is also especially remarkable in monoclonal antibodies produced by hybridoma 9A3 and 20D11.

Moreover, as seen from Table 4, in addition to stomach cancer cells, the present monoclonal antibodies react with cancer cells from other organs including cells of lung cancer, breast cancer, cancer of the tongue, cancer of the esophagus, duodenal cancer, bile duct cancer, carcinoma of skin, colon cancer, and salivary gland cancer, etc.

The present invention will now be further explained by, but is by no means limited to, the following examples.

EXAMPLE 1

(1) Preparation of Parent Cells

Balb/c mice were immunized by intraperitoneal injection of $10^6$ cells of poorly-differentiated human stomach adenocarcinoma cell line TMK-1, and were boosted twice every ten days after the first immunization. Three days after the last boost, spleens were removed from the immunized mice, and were teased to suspend splenocytes in an RPMI-1640 medium, which splenocytes were then filtered through a nylon mesh filter to prepare a mouse splenocyte suspension at a concentration of $2 \times 10^6$ cells/ml.

A suspension of mouse tumor cells P3U1 (Flow) in RPMI-1640 medium was prepared according to a conventional method.

(2) Cell Fusion

The suspension of mouse splenocytes prepared as above, and the suspension of P3U1 cells prepared as above, were mixed in a test tube at a ratio of cell numbers of splenocytes and P3U1 cells of 10:1, and the mixture was centrifuged to separate a cell pellet and a supernatant, which supernatant was then removed and discharged. The cell pellet on the bottom of the test tube was gradually added dropwise with 1 ml of PSB(−) (8.0 g sodium chloride, 0.2 g monopotassium dihydrogen phosphate anhydride, 1.5 g disodium hydrogen phosphate anhydride, 0.2 g potassium chloride in 1000 ml water) containing 40% of polyethylene glycol (PEG) having a molecular weight of 4000. The mixture was allowed to stand for four minutes at a temperature of 37° C., and then added with 30 ml of RPMI-1640 medium supplemented with 10% FCS to dilute the PEG. The diluted mixture was then centrifuged to remove a supernatant, the remaining cells were diluted with an RPMI-1640 medium supplemented with 10% FCS to a concentration of $1.0 \times 10^5$ cells/ml, and 100 µl of the suspension was distributed to each well of a 96-well plate, which well has been previously added with 100 µl of a suspension containing $5 \times 10^5$ of thymus cells derived from a three-week old Balb/c mouse as feeder cells.

(3) Selection of Hybridoma

Starting from the day after the fusion, half of the medium (100 µl) was exchanged with the same volume of an HAT medium every day for four days. Subsequently, the exchanges were carried out every two days. The culturing was continued for a total of ten days. The above-mentioned HAT medium is an RPMI-1640 medium supplemented with 100 µM hypoxanthine, 0.1 µM aminopterin, 1.6 µM thymidine, 10% FCS, $5 \times 10^{-5}$ M 2-mercaptoethanol, 2 mM glutamine, 100 U/ml penicillin, and 0.1 mg/ml streptomycin (pH 7.4).

The supernatant was analyzed as follows:

(a) Preparation of Plate for Assay

Preparation of Antigen

TMK-1 cells were suspended in a Tris-HCl buffer (pH 7.4) containing 0.25 M sucrose, the suspension was homogenized, and the homogenate was centrifuged to remove a supernatant. The precipitate was resuspended in the same buffer, and the suspension was centrifuged to remove a supernatant. The precipitate was resuspended in PBS to obtain a cell suspension at a concentration of $2 \times 10^6$ cells/ml. The PBS was PBS(−) supplemented with 1.0 g/l calcium chloride and 1.0 g/l magnesium chloride.

Immobilization of Antigen

50 µl of PBS(−) supplemented with 10 µg/ml poly-L-lysine were distributed to each well of a 96-well plate (Falcon), the plate was allowed to stand for 30 minutes at a room temperature, and was then washed with PBS(−)-Tween (supplied by Wako). The PBS(−)-Tween is (PBS)(−) supplemented with 0.5 ml/l Tween 20. To each of the wells was added 50 µl of the antigen prepared as above, and the plate was centrifuged to remove a supernatant. Each of the wells was then added with 50 µl of PBS(−) supplemented with 0.5% glutaraldehyde, incubated for 15 minutes at a room temperature, and washed twice with TBS(−)-Tween. Each of the wells was then added with 50 µl of PBS(−) supplemented with 1% bovine serum albumin (BSA) and 100 mM glycine, incubated for 30 minutes at a room temperature, and washed once with PBS(−)-Tween. Each of the wells was then added with 250 µl of PBS(−) supplemented with 1% BSA, incubated for two hours at a room temperature, and washed with PBS(−)-Tween.

A control plate was prepared by using normal stomach mucous membranes cells instead of TMK-1 cells, under the same procedure as above.

(b) Assay of Supernatant

A supernatant was sampled from the wells in which a colony was formed, and 50 µl of the sample was added to a well of each of two plates prepared as above. The plates were incubated for two hours, and washed three times with PBS(−)-Tween. 50 µl of a peroxidase-labeled goat anti-mouse immunoglobulin (Kirkegaard and Perry Lab) was added to each well, and the plates were incubated for two hours at a temperature of 37° C. in the presence of 5% carbon dioxide. After four times of washing with PBS(−)-Tween, each well was added with 100 µl of a substrate solution for an assay of enzyme activity fixed to the plate. The substrate solution was 0.1 M of a citrate buffer containing 2.5 mM 2,2'-azinobis(3-ethylbenzothiazoline)-6-sulphonic acid (ABTS) and 5 mM hydrogen peroxide, and was prepared immediately before use. The enzyme reaction was carried out for 5 to 15 minutes and terminated by the addition of 100 µl/well of 2 mM sodium azide, and absorption at 405 mm ($OD_{405}$) was measured with a Titertek Multiscan (T.M.) (Flow).

By this method, ten wells whose supernatants react with a plate on which TMK-1 cells have been immobilized but do not react with a plate on which normal stomach mucous membranes cells have been immobilized, were selected. Colonies from the ten wells were picked up, and cloned by a limiting dilution method to establish ten hybridoma.

(4) Culturing of Hybridoma and Recovery of Monoclonal Antibody

Each of ten hybridoma obtained as above was cultured in 100 ml of an RPMI-1640 medium supplemented with 10% FCS at a temperature of 37° C. in the presence of 5% carbon dioxide in a carbon dioxide incubator for 4 days. After the culturing, monoclonal antibodies were recovered from the supernatants by ammonium sulfate precipitation. The recovered monoclonal antibodies were characterized as shown in Table 1.

TABLE 1

| Hybridoma | Subclass |
|---|---|
| 6D3 | IgM/κ |
| 10H9 | IgM/κ |
| 21A4 | IgM/κ |
| 17F11 | IgM/κ |
| 9A3 | IgG$_1$/κ |
| 1H8 | IgM/κ |
| 4H11 | IgM/κ |
| 8A10 | IgM/κ |
| 1D12 | IgM/κ |
| 20D11 | IgM/κ |

*IgM/κ shows that the subclass of the corresponding monoclonal antibody is IgM and the light chain is κ (kappa). Similarly, IgG$_1$/κ shows that the subclass of the corresponding monoclonal antibody is IgG$_1$ and the light chain is κ (kappa).

EXAMPLE 2

Three monoclonal antibodies produced by hybridomas 9A3, 20D11, and 21A4 were characterized by their specificity to stomach cancer cells. The specificity was determined with Vectastain (T.M.) ABC kit as follows.

Stomach cancer tissue sections obtained from human patients (55 cases) were incubated in methanol containing 0.3% hydrogen peroxide to block peroxidase activity present in the tissue. The tissue sections were then washed with PBS(−), incubated with normal horse serum diluted 20 times with PBS(−), and washed with PBS (−). The sections were then incubated with biotinated horse anti-mouse immunoglobulin (Vector) at a room temperature for 60 minutes, and then washed with PBS(−). The sections were then incubated with avidin and biotinated peroxidase conjugate for 60 minutes at a room temperature, and washed with PBS(−). The sections were then added with a solution containing diaminobenzidin and hydrogen peroxide, and incubated for five minutes, washed with PBS(−), and stained with methyl green. The results are set forth in Table 2. In Table 2, 9A3, 20D11, and 21A4 represent hybridomas which produced tested monoclonal antibodies.

In Table 2, the expression histological typing is in accordance with the general rules for the gastric cancer study in surgery and pathology by Japanese Research Society for gastric cancer, and has the following meaning:

pap: papillary adenocarcinoma
  tub$_1$: well-differentiated tubular adenocarcinoma
  tub$_2$: moderatly-differentiated tubular adenocarcinoma
  por: poorly-differentiated adenocarcinoma
  sig: signet ring cell carcinoma
  muc: mucinous adenocarcinoma
  sq: squamous cell carcinoma Further, (med) represents medullary carcinoma, and (sci) represents scirrhous carcinoma. The symbols +, ±, and −, have the following meanings:

+: strongly stained
  ±: partially stained
  −: not stained

TABLE 2

| Case No. | Histological typing | 9A3 | 20D11 | 21A4 |
|---|---|---|---|---|
| 1 | por | + | + | + |
| 2 | por | + | + | + |
| 3 | tub$_2$ | + | + | + |
| 4 | por | + | ± | + |
| 5 | por(sci) | + | + | + |
| 6 | tub$_2$(med) | + | ± | + |
| 7 | tub$_2$ | + | + | + |
| 8 | por(sci) | + | + | + |
| 9 | por | + | + | + |
| 10 | por(sci) | + | + | + |
| 11 | sig | + | − | + |
| 12 | tub$_2$(sci) | + | − | + |
| 13 | por(med) | + | + | + |
| 14 | por(sci) | + | − | + |
| 15 | tub$_1$ | + | − | + |
| 16 | tub$_2$ | + | + | + |
| 17 | sig | + | − | ± |
| 18 | sig(sci) | + | − | − |
| 19 | tub$_2$ | + | − | + |
| 20 | tub$_1$ | + | + | − |
| 21 | por | + | − | + |
| 22 | tub$_2$ | + | + | + |
| 23 | por(sci) | + | − | ± |
| 24 | por | + | − | + |
| 25 | sq | + | + | + |
| 26 | muc(med) | + | − | + |
| 27 | tub$_2$ | + | ± | + |
| 28 | por(sci) | + | + | + |
| 29 | sig(sci) | + | + | + |
| 30 | por | + | − | − |
| 31 | muc | + | − | + |
| 32 | por(sci) | + | + | + |
| 33 | tub$_1$ | + | + | + |
| 34 | pap | + | + | + |
| 35 | por(sci) | + | − | + |
| 36 | por(sci) | + | + | + |
| 37 | por | + | + | + |
| 38 | por | + | − | + |
| 39 | tub$_2$ | + | + | + |
| 40 | muc | + | − | + |
| 41 | tub$_1$ | + | + | − |
| 42 | pap | + | + | + |
| 43 | tub$_2$ | + | + | − |
| 44 | tub$_2$ | + | − | + |
| 45 | pap | + | + | + |
| 46 | tub$_2$ | + | + | + |
| 47 | muc | + | − | + |
| 48 | tub$_2$ | + | + | + |
| 49 | tub$_{1(med)}$ | + | + | + |
| 50 | por(med) | + | + | ± |
| 51 | por(sci) | + | + | − |
| 52 | por(sci) | + | − | + |
| 53 | tub$_1$ | ± | − | + |
| 54 | por(med) | + | − | ± |
| 55 | por(sci) | + | + | + |

EXAMPLE 3

Reaction of monoclonal antibodies produced by hybridomas 9A3, 20D11, and 21A4 with normal cells was tested by the procedure described in Example 2.

The Results are set forth in Table 3.

TABLE 3

| Organ or Tissue | | Monoclonal antibody produced by | | |
|---|---|---|---|---|
| | | 9A3 | 20D11 | 21A4 |
| Lung | Bronchial epithelium | − | − | + |
| | Cartilage | − | − | − |
| | Glandular epithelium | − | − | − |
| | Alveolar epithelium | − | + | − |
| | Connective tissue | − | − | − |
| | Bulla | − | + | − |
| Spleen | White pulp | − | − | − |
| | Red pulp | +* | − | − |
| Liver | Liver cell | − | − | − |
| | Colangiolar epithelium | − | − | + |
| | Sinusoid | − | − | − |
| Gallbladder | | − | − | + |
| Tongue | | − | − | − |

TABLE 3-continued

| Organ or Tissue | | 9A3 | 20D11 | 21A4 |
|---|---|---|---|---|
| Esophagus | | − | − | − |
| Stomach | Body | − | + | + |
| | Pyloric part | − | − | − |
| Small intestine | | − | − | ± |
| Colon | Sigmoid colon | − | ± | ± |
| Pancreas | Exocrine gland | − | ± | + |
| | Endocrine gland | − | + | − |
| Kidney | Glomerulus | − | − | − |
| | Proximal uriniferous tubule | − | + | − |
| | Loop of Henle | − | − | − |
| | Distal uriniferous tubule | − | − | − |
| | Collecting tubule | − | + | − |
| Sialaden | | − | − | + |
| Adrenal body | Adrenal cortex | − | − | − |
| | Medulla glandulae | − | − | − |
| Thyroidea | Thyroid epithelium | − | ± | − |
| | Thyroid colloid | − | − | − |
| Parathyroid | | − | − | − |
| Prostate | Epithelium | − | + | + |
| | Matrix | − | − | − |
| Ovarium | Germ cell | − | − | − |
| | Connective tissue | − | − | − |
| Uterus | Endometrium | − | + | + |
| | Myometrium | − | − | − |
| Placenta | Trophoblast cell | − | ± | ± |
| | Syncytiotrophoblast | − | − | − |
| Skin | Sinusoid | − | + | − |
| | Epidermis | − | − | − |
| | Melanoblast | − | − | − |
| | Glandulae sudoriferae | − | − | − |
| | Sebaceous gland | − | + | − |
| | Dermis | − | − | − |
| Brain | Neuron | − | − | − |
| | Gliacyte | − | − | − |
| | Dendrite | − | − | − |
| Lymphoglandula | Lymphonodi | − | − | − |
| Blood vessel | Endothelium | − | − | − |
| | Smooth muscle | − | − | − |
| Capillary vessel | | − | − | − |
| Skeltal muscle | | − | − | − |
| Parenchyma | | − | − | − |
| Glandula mammaria | Excretory duct | − | + | + |
| | Matrix | − | − | − |
| Pituitary gland | | − | − | + |
| Nervous system | Automatic nervous system | − | − | − |

EXAMPLE 4

The reactivity of monoclonal antibodies produced by hybridomas 9A3, 20D11, and 21A4 with cancer cells of various tissues was tested by the procedure described in Example 2. The results are set forth in Table 4.

TABLE 4

| | Kind of cancer | 9A3 | 20D11 | 21A4 |
|---|---|---|---|---|
| Nervous system | Fibrous astrocytoma | − | − | − |
| | Astrocytoma | − | − | − |
| | Neuroblastoma (Mediastinum primary) | − | − | − |
| | Medulloblastoma | − | − | − |
| | Glioblastoma multiforme | − | − | − |
| Pituitary gland | Eospinophil adenoma | − | − | − |
| | Basophil adenoma | − | − | − (Partially) |
| | Chromophobe adenoma | − | − | − |
| Thyroid body | Thyroid medullary carcinoma | + | − | − |
| | Thyroid medullary carcinoma | − | − | − |
| Accessory parathyroid | Adenoma | − | − | − |
| Lung | Squamous cell carcinoma | + | + | − |
| | Adenocarcinoma | + | + | + |
| | Carcinoid | − | − | − |
| Breast cancer | Signet ring cell carcinoma | + | + | + |
| | Infiltrating duct carcinoma | − | + | + |
| | | − | + | − |
| | | − | − | − |
| | | + | + | + |
| | Adenoma of nipple | − | − | − |
| | Benign hypertrophy | − | + | + |
| | Fibroadenoma | − | + | + |
| | Solid tubular adenocarcinoma | − | + | − |
| Tongue | Squamous cell carcinoma | + | + | − |
| Esophagus | Poorly differentiated squamous cell carcinoma | + | − | + |
| Duodenum | Adenocarcinoma | + | + | + |
| | Duodenal carcinoid | + | + | + |
| Cystic duct/pancreas | Choledocnal adenocarcinoma | + | + | + |
| Kidney | Renal cell carcinoma | − | − | − |
| Urogenital | Transitional cell carcinoma (bladder) | − | + | + |
| | Adenocarcinoma (prostate) | + | − | − |
| | Adenocarcinoma (cervix uteri) | + | + | + |
| | Endometrium carcinoma | + | + | + |
| | Destructive mole | − | + | + |
| | Clear cell carcinoma | − | + | + |
| | Hydatidiform mole | − | − | + |

TABLE 4-continued

| | Kind of cancer | Monoclonal antibody produced by | | |
|---|---|---|---|---|
| | | 9A3 | 20D11 | 21A4 |
| | Mucous cystadenocarcinoma | + | — (partially +) | + |
| Adrenal body | Adrenal cortical carcinoma | — | — | — |
| Skin | Paget disease | + | + | — |
| Lymphatic system | Malignant lymphoma | — | — | — |
| Bone/cortilage | Osteosarcoma | — | — | — |
| | Condrosarcoma | — | — | — |
| Large intestine | Well differentiated adenocarcinoma | + | + | + |
| | Adenocarcinoma | + | + | + |
| Sialaden | Adenoid cystic carcinoma | + | + | + |

As seen from Examples 2 to 4, monoclonal antibodies according to the present invention react with human cancer cells but do not react substantially with normal cells. Therefore, the monoclonal antibodies can be used for the diagnosis of cancer. In such a diagnosis, a monoclonal antibody conjugated with label material such as an enzyme, fluorescent material, etc., is reacted with a sample suspected to contain cancer cells, and the label which binds through the monoclonal antibody to the cancer cells is detected. Alternatively, a monoclonal antibody conjugated with metal protein such as ferritin, which produces an electron interference, is reacted with a sample. In this case, cancer cells can be detected with a electron microscope.

As monoclonal antibodies of the present invention react with cancer cells from more than one human organ, one monoclonal antibody can be used to diagnose cancer from more than one organs. Moreover, as monoclonal antibodies of the present invention react with cancers having various differentiation extents, including poorly-differentiation, these antibodies can be used for the diagnoses of cancer having from a poorly-differentiation to a well-differentiation.

Monoclonal antibodies produced by hybridomas 9A3, and 20D11 notably show the above-mentioned characteristics. As these antibodies react relatively strongly with stomach cancer cells but substantially do not react with normal cells except for neutrophil leucocyte and macrophage, they are especially useful for the diagnosis of stomach cancer.

Moreover, monoclonal antibodies of the present invention, in combination with a chemotherapeutic agent for cancer therapy, may be used for a so-called missile therapy wherein the monoclonal antibody selectively directs the agent to the cancer cells (*British Medical Journal*), 285, 461–462, 1982; and 285, 1447, 1982).

The preferable hybridoma cell lines of the present invention are 9A3, which was designated as SCI 9A3 (ATCC Accession No. HB 8988), and 20D11, which was designated as SCI 20D11 (ATCC Accession No. HB 8989), (for both hybridoma cell lines, accession numbers not received prior to filing, but deposit questionnaire forms mailed to ATCC from Japan on Aug. 24, 1985); which were deposited to Institute of Fermentation, Osaka (IFO), 17-85 Juso-honmachi 2-chome Yodogawa-ku, Osaka, Japan, on Oct. 18, 1985, as IFO-50061 and IFO-50062 respectively. The cell lines designated as ATCC accession numbers HB 8988 and HB 8989 were deposited with the American Type Culture Collection, 12301 Park Lawn Drive, Rockville, Md. 20852, on Nov. 27, 1985.

We claim:

1. A monoclonal antibody against human cancer, produced by a hybridoma selected from the group consisting of 9A3, and 20D11.

2. A hybridoma cell line capable of producing a monoclonal antibody against human cancer selected from the group consisting of 9A3 and 20D11.